(12) United States Patent
Chen et al.

(10) Patent No.: US 11,260,101 B2
(45) Date of Patent: Mar. 1, 2022

(54) REPAIR PEPTIDE FOR USE IN PROMOTING POST-TRAUMATIC TISSUE REPAIR AND REGENERATION, AND APPLICATION THEREOF

(71) Applicant: Jinan University, Guangdong (CN)

(72) Inventors: Xiaojia Chen, Guangdong (CN); An Hong, Guangdong (CN)

(73) Assignee: Jinan University, Guangdong (CN)

( * ) Notice: Subject to any disclaimer, the term of this patent is extended or adjusted under 35 U.S.C. 154(b) by 72 days.

(21) Appl. No.: 16/483,996

(22) PCT Filed: Feb. 26, 2018

(86) PCT No.: PCT/CN2018/077232
§ 371 (c)(1),
(2) Date: Aug. 6, 2019

(87) PCT Pub. No.: WO2018/157773
PCT Pub. Date: Sep. 7, 2018

(65) Prior Publication Data
US 2020/0000868 A1   Jan. 2, 2020

(30) Foreign Application Priority Data

Feb. 28, 2017 (CN) .......................... 201710112907.0
Feb. 9, 2018 (CN) .......................... 201810135019.5

(51) Int. Cl.
*A61K 38/00* (2006.01)
*A61K 38/04* (2006.01)
*A61P 17/00* (2006.01)

(52) U.S. Cl.
CPC .............. *A61K 38/04* (2013.01); *A61P 17/00* (2018.01)

(58) Field of Classification Search
CPC .......... A61K 38/04; A61K 38/00; A61K 8/64; A61P 17/00; A61P 17/02; A61Q 19/00; C07K 7/06; C07K 7/08
See application file for complete search history.

(56) References Cited

U.S. PATENT DOCUMENTS

| 4,957,738 A | 9/1990 | Patarroyo | |
|---|---|---|---|
| 2006/0025524 A1* | 2/2006 | Schneider | A61K 47/48 525/54 |

FOREIGN PATENT DOCUMENTS

| CN | 1305495 A | 7/2001 | |
|---|---|---|---|
| CN | 101152568 | 4/2008 | |
| CN | 101378772 | 3/2009 | |
| CN | 102724992 | 10/2012 | |
| CN | 103980349 A | 8/2014 | |
| WO | WO200166689 A2 * | 9/2001 | ......... C07K 14/8107 |
| WO | WO200175067 A2 * | 10/2001 | ......... C07K 14/8107 |
| WO | WO 200179449 A2 * | 10/2001 | ......... C07K 14/8107 |

OTHER PUBLICATIONS

Chinese Search Report for Application No. 201810135019.5 dated Feb. 9, 2018.
Chinese Office Action for Application No. 201810135019.5 dated Apr. 1, 2020.

* cited by examiner

*Primary Examiner* — Christina Bradley
*Assistant Examiner* — Mercy H Sabila
(74) *Attorney, Agent, or Firm* — Simpson & Simpson, PLLC; Michael Nicholas Vranjes (57) ABSTRACT

Provided are a repair peptide for use in promoting post-traumatic tissue repair and regeneration, and an application thereof. The repair peptide is a linear or cyclic peptide which is 4-15 amino acids in length and which contains four or more consecutive GPANVET core sequences.

1 Claim, 6 Drawing Sheets

Specification includes a Sequence Listing.

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial sequence
<220> FEATURE:
<223> OTHER INFORMATION: R1

<400> SEQUENCE: 1

Gly Pro Ala Asn Val Glu Thr
1               5

<210> SEQ ID NO 2
<211> LENGTH: 13
<212> TYPE: PRT
<213> ORGANISM: Artificial sequence
<220> FEATURE:
<223> OTHER INFORMATION: R2

<400> SEQUENCE: 2

Lys Val Lys Val Gly Pro Ala Asn Val Lys Val Lys Val
1               5                   10

<210> SEQ ID NO 3
<211> LENGTH: 11
<212> TYPE: PRT
<213> ORGANISM: Artificial sequence
<220> FEATURE:
<223> OTHER INFORMATION: R3

<400> SEQUENCE: 3

Gly Pro Ala Asn Val Glu Lys Glu Lys Glu Lys
1               5                   10

<210> SEQ ID NO 4
<211> LENGTH: 9
<212> TYPE: PRT
<213> ORGANISM: Artificial sequence
<220> FEATURE:
<223> OTHER INFORMATION: R4

<400> SEQUENCE: 4

Cys Gly Pro Ala Asn Val Glu Thr Cys
1               5

<210> SEQ ID NO 5
<211> LENGTH: 5
<212> TYPE: PRT
<213> ORGANISM: Artificial sequence
<220> FEATURE:
<223> OTHER INFORMATION: consecutive amino acids

<400> SEQUENCE: 5

Gly Pro Ala Asn Val
1               5
```

```
<210> SEQ ID NO 6
<211> LENGTH: 6
<212> TYPE: PRT
<213> ORGANISM: Artificial sequence
<220> FEATURE:
<223> OTHER INFORMATION: consecutive amino acids

<400> SEQUENCE: 6

Gly Pro Ala Asn Val Glu
1               5
```

REPAIR PEPTIDE FOR USE IN PROMOTING POST-TRAUMATIC TISSUE REPAIR AND REGENERATION, AND APPLICATION THEREOF

CROSS-REFERENCE TO RELATED APPLICATIONS

The present application is the United States National Stage Application pursuant to 35 U.S.C. § 371 of International Patent Application No. PCT/CN2018/077232, filed on Feb. 26, 2018, which application claims priority to Chinese Patent Application No. 201810135019.5 filed on Feb. 9, 2018, and Chinese Patent Application No. 201710112907.0 filed on Feb. 28, 2017, which applications are incorporated herein by reference in their entireties.

REFERENCE TO A SEQUENCE LISTING

The content of the ASCII text file of the sequence listing named "BETP101US sequence listing" which is 2 KB in size, was created on Apr. 22, 2021 and electronically submitted herewith is incorporated herein by reference in its entirety.

TECHNICAL FIELD

The present invention relates to a field of biomedicine and, in particular, to a repair peptide for use in promoting post-traumatic tissue repair and regeneration, and an application thereof, especially the application in tissue repair and regeneration in skin damage and nerve damage. The peptide may promote tissue repair and cell proliferation in a wound site.

BACKGROUND

Many factors will cause cell and tissue damages. The healthy cells that survive in a damaged tissue and its vicinity continue to divide and proliferate to replace the dead cells and repair the damaged tissue. This physiological function of the organism is called regeneration and repair.

Normally, the repair and regeneration capability of different human organs is different. Epidermal cells (such as cover epitheliums of mucosae of the respiratory tract, digestive tract and genitourinary tract), lymphocytes, hematopoietic cells, etc. are aging and rejuvenating all the time, and have a strong regeneration and repair ability against damage, so they are cells with a strong regeneration ability. Other cells, such as vascular endothelial cells, periosteal cells, cells of various glandular organs (including the liver, pancreas, endocrine gland, sweat gland and sebaceous gland) and renal tubular epithelial cells, which belong to cells with a relative lower regeneration ability, also show a certain regeneration ability when damaged. As specifically reflected in a local tissue, when such normal cells are destroyed, residual cells will divide and replenish this tissue; but when the cells in the local tissue are completely destroyed and the cells are completely necrotic, this local tissue cannot be repaired. In addition, there are cells with weak or no regeneration ability. For example, central nervous cells and ganglion cells have a weak regeneration ability, and their original functions are difficult to restore after being damaged. Cardiomyocytes have an extremely weak regeneration ability, and they will be replaced by fibrous connective tissues and their original structures and functions are difficult to restore after being damaged.

Many factors will affect the tissue regeneration. Besides the regeneration ability of the tissue and cell themselves, there are several factors: (1) the degree and area of tissue damage: the larger the degree or area is, the more time the repair and regeneration need. This is because necrotic cells are hardly replaced by considerable cells of the same type when a wide area of cellular necrosis occurs, in which case healthy cells are required to generate new cells, and the nascent cells are again required to generate new cells, which takes a long time; (2) age factor: children and adolescents have a strong regeneration ability and the wound will be healed rapidly while the tissue regeneration ability of the elderly is weak and the wound is healed slowly; (3) nutritional condition: adequate supply of protein, vitamins C and E and minerals such as calcium and zinc can promote the repair of damage, otherwise the repair of various damages will be delayed; (4) drug effect: some drugs such as adrenocortical hormone and pituitary adrenocorticotropic hormone can inhibit inflammation, inhibit granulation tissue growth and collagen synthesis, and accelerate collagen decomposition, but are not conducive to the body to eliminate wound infection; and cytotoxic anticancer drugs can also delay the healing; (5) blood supply: after the tissue is damaged, the angiosclerosis caused by local capillary damage or other factors may result in insufficient blood supply, which causes tissue malnutrition and hinders the healing; and (6) innervation: the tissue that loses the innervation will lose its regeneration ability.

It can be seen from the above that other than objective factors such as the age that cannot be interfered, after the body tissue is damaged, the proliferation of viable cells, the neogenesis of capillaries and the regeneration of nerve cells can be promoted by increasing the nutrient supply to the damaged site and adopting drug intervention to speed up the tissue repair.

Wound repair in the three major application areas of current tissue repair: skin tissue, nerve tissue and bone tissue will be described below in detail.

1. Wound Repair of the Skin Tissue

The skin is the tissue which has the largest area of the human body and contacts the outside world most directly, but is also an organ most vulnerable to external stimuli. The normal wound healing is essential for maintaining homeostasis in the body. However, abnormal healing, such as disunion or delayed healing caused by large-scale burns, chronic wound healing caused by other diseases, formation of pathological scars that are unable to be normally healed, and the like, not only affects the appearance, but also causes structural and functional obstacles, which often brings great psychological pressure to the patient, and seriously affects the patient's physical and mental health. Therefore, how to quickly achieve the best healing effect in the skin wound treatment has been a hot research issue.

The healing of the skin is a complex, coordinated and orderly process of tissue repair and regeneration, a process in which a variety of cells and cytokines cooperate. This process may be generally divided into three phases: inflammatory reaction phase, proliferative phase and remodeling phase. There are no strict boundary between the three phases, and a large number of cells and cytokines participate in the healing process. The cells participating in the healing include keratinocytes, vascular endothelial cells, fibroblasts, neutrophils, monocytes/macrophages, mast cells and the like. The cytokines participating in the healing include fibroblast growth factor (FGF), vascular endothelial growth factor (VEGF), platelet derived growth factor (PDGF), tumor necrosis factor-α (TNF-α), transforming growth factor (TGF), insulin-like growth factor (IGF) and various blood coagulation factors. Cells secrete cytokines to regulate the wound healing, and the cytokines in turn affect functions of the cells. Since abnormalities in any one of the processes may cause abnormal skin healing, and the skin healing process is affected by many factors (age, nutritional condition, endocrine changes, drugs, local blood circulation, infection, ionizing radiation, systemic diseases, etc.), the mechanism of skin healing is still not completely clear.

At present in clinical, the skin wound repair involves different medications and treatments based on whether acute skin and soft tissue wounds or chronic skin and soft tissue wounds are needed to be healed. Based on the advantages of traditional Chinese medicine in China, many single drugs such as Kangfuxin Solution, and compound drugs, which are prepared from a combination of Chinese medicines varying from four or five to twenty or thirty, such as Moisture exposed burn ointment (MEBO), Jingwanhong Soft Plaster and other drugs for treating the burns, have emerged in the field of wound repair. After the modern medicine, especially the biomedical medicine involved by genetic engineering technology, is developed, the production of recombinant growth factors for promoting the cell growth has also become a new force in the development of wound repair drugs. For example, a biotech drug, topical recombinant basic Fibroblast Growth Factor (bFGF, also known as fibroblast growth factor-2 (FGF2)), is the second genetically engineered Class 1 new drug in China, which has been clinically applied to the treatment of wounds and burns.

In the development of peptide drugs for skin repair, in 2014, Kunming Institute of Zoology of the Chinese Academy of Sciences reported a skin repair peptide (Tylotoin) derived from salamander, which contains 12 amino acid residues and shows strong wound-healing-promoting activity. Tylotoin can promote the proliferation and migration of epithelial keratinocytes and fibroblasts, and promote the generation of TGF-b and IL-6. Chinese patents have also disclosed peptides for promoting the skin repair, which are extracted from the South China tree-frog, Tylototriton shanjing and Odorrana graham and respectively are 16 peptides, 13 peptides, 24 and 11 peptides.

2. Wound Repair of the Never Tissue

The nervous system is a functional regulation system that plays a leading role in the human body. The functions and physiological processes of various organs and systems of the human body are directly or indirectly regulated and controlled by the nervous system, to connect, interact and closely cooperated with each other, thereby achieving and maintaining normal life activities. At the same time, the nervous system of the human body can sense the changes in the external environment, accept information about changes in the internal and external environments, and constantly and thoroughly adjust various functions in the body, so as to enable the human body to adapt to changes in the internal and external environments.

The nervous system consists of a central part and a peripheral part. The central part includes the brain and the spinal cord, which are respectively located in the cranial cavity and the spinal canal. The two are closely related in structure and function and form the central nervous system. The peripheral part includes 12 pairs of cranial nerves and 31 pairs of spinal nerves, which form the peripheral nervous system. The peripheral nerves are distributed throughout the body and link the brain and spinal cord to other organs of the body, allowing the central nervous system to sense changes in both internal and external environments (transporting sensory information through afferent nerves) and regulate various functions in the body (delivering regulation instructions through efferent nerves), thereby ensuring the integrity of the human body and adapting the body to the environment.

The central nervous system composed of the human brain and spinal cord lacks self-regeneration and repair ability. There is no effective treatment for the cell death, tissue destruction and permanent neurological deficits caused by the damage of the central nervous system.

The peripheral nerve injury is divided into an open injury and a non-open injury. The former is generally associated with the open injury of soft tissue, causing partial or complete truncation of the nerve; and the latter is complicated by the blunt non-open injury of soft tissue, causing contusion, compression or stretch of the nerve trunk which causes small hemorrhage and edema and myelin edema and degeneration in the nerve. The result of the peripheral nerve injury is mainly manifested clinically as neurological paralysis, and the occurrence of sensory disturbance, dyskinesia and muscle atrophy in the area innervated by the nerve.

The clinical drugs for nerve injury generally include two major types. The first one is the nerve growth factor enhancer, including: 1. Leteprinim, which is a cognitive enhancer for the treatment of mild to moderate Alzheimer's disease (AD), and can enhance the neuronal function, stimulate the axon growth, and improve memory by increasing the neurotrophic growth factor level in damaged or degenerated neurons, becoming the first drug for enhancing nerve regeneration to enter phase III clinical trials; and 2. acetyl L-carnitine, which is a cholinergic agonist and can actively pass through the blood brain barrier, protect central and peripheral synapses in neurodegenerative and aging models, increase nerve growth factor levels, and improves the recognition defect of aged rats, currently undergoing Phase III clinical trials in America. The second one is the neurotrophic drug, including: 1. gangliosides (GM1), which promotes nerve remodeling (including nerve cell survival rate, axonal elongation and synaptic growth), and plays an important role in cell differentiation, development, nerve tissue repair, neuronal plasticity and other aspects; 2. cerebral protein hydrolysate, which is a new drug for improving brain metabolism and can easily pass through the blood-brain barrier to enter the brain nerve cells, affect protein synthesis and respiratory chain of brain cells, enhance the antioxidant capacity of brain cells, protect the nervous system from toxic substances, delay the brain cell death and increase their survival rate; 3. cytidine disodium triphosphate injection, which is a nucleotide drug and can promote the protein synthesis, regulate and promote the synthesis and construction of membranous structures of nerve cells, neural glial cells and vascular wall cells, and fight against never cell injury caused by excitatory amino acids and free radicals, thereby supporting the cell survival, enhancing the cell activity, delaying the cell death, improving the cell anti-damage and repair ability, promoting the axonal regrowth, improving the nerve function for innervating blood vessels, and resisting the angiosclerosis; and 4. oxiracetam, which is a novel central nervous system drug for promoting the learning and memory ability and can activate, protect or promote the function recovery of nerve cells by selectively acting on the cerebral cortex and hippocampus.

SUMMARY

In order to solve deficiencies in the prior art, a primary object of the present invention is to provide a short peptide for use in promoting post-traumatic tissue repair and regeneration, which is named as the repair peptide. The present invention provides a short peptide consisting of 4-15 amino acid residues. The short peptide is multiple linear peptides and cyclic peptides derived from the sequence GPANVET (SEQ ID NO:1), which are temporarily named as the repair peptide. The peptide sequence is obtained by multiple rounds of screening and identification in a phage peptide library (7-peptide library) by using the extramembranous segment of fibroblast growth factor receptor 2 (FGFR2) as a target point. So far, no literature has reported that this peptide can be used for skin wound repair and nerve injury repair.

Another object of the present invention is to provide an application of the repair peptide as described above for use in the repair and regeneration of skin wound and nerve injury.

The objects of the present invention are implemented through a technical solution described below.

The object of the present invention is to provide a repair peptide for use in promoting post-traumatic tissue repair and regeneration. The repair peptide is a linear or cyclic peptide which contains four or more consecutive amino acids of the core sequence GPANVET (SEQ ID NO:1) and which is 4-15 amino acids in length.

Specifically, an R1 peptide of the repair peptide has the sequence of GPANVET (SEQ ID NO:1), an R2 peptide thereof has the sequence of KVKVGPANVKVKV (SEQ ID NO:2), an R3 peptide thereof has the sequence of GPANVEKEKEK (SEQ ID NO:3), and an R4 peptide thereof has the sequence of CGPANVETC (SEQ ID NO:4).

The R1 peptide only contains the core sequence GPANVET (SEQ ID NO:1); the R2 peptide contains five consecutive amino acids (GPANV (SEQ ID NO:5)) of the core sequence; the R3 peptide contains six consecutive amino acids (GPANVE (SEQ ID NO:6)) of the core sequence; and the R4 peptide contains all seven amino acids of the core sequence, and forms a cyclic peptide through a disulfide bond between two cysteines at both ends.

These repair peptides of the present invention can be obtained through chemical synthesis.

The object of the present invention is to provide an application of the repair peptide in preparation of a product for tissue regeneration and repair of skin damage and never injury, especially the application in the preparation of a product for skin wounds, burns, chronic wound healing, skin cell repair and regeneration, central nervous injury caused by brain injury, stroke, cerebral edema and cerebral hypoxia, and nerve injury repair and regeneration of sensory disturbance, dyskinesia and dystrophy caused by peripheral nerve injury.

The product preferably is a medical product, a skin care product or a cosmetic product.

The formulation type of the product preferably is, but not limited to, a solution, a lyophilized formulation, an emulsion, a cream, a gel, a mask, a dressing or the like.

The content of the present invention is experiments on mouse fibroblasts balb/c 3T3, human umbilical vein endothelial cells (HUVEC), chick embryo chorioallantoic membranes, and animal models of mice and rats.

Compared with the related art, the present invention has following advantages and effects.

Compared with the current similar product, topical recombinant bFGF (including 155 amino acids), the repair peptide provided by the present invention can also be combined with the membrane receptor FGFR2, and has a comparable effect of promoting skin wound repair and nerve injury repair and regeneration, but has a smaller molecular weight, and adopts a chemical synthesis method instead of a genetic engineering method, so in the use condition with the same molar concentration, the required production cost and use cost are lower. Therefore, it is a good wound repair and cell regeneration and proliferation product which can replace the recombinant bFGF. The recombinant bFGF has serious requirements for storage and transportation in vitro and is easily degradable, which causes its low accumulation and unsustainable effect in treatment sites, thus restricting and affecting its use and related dosage form development to some extent. Compared with growth factors such as bFGF, NGF and BDNF, the degradation degree of the repair peptides provided by the present invention is greatly reduced because they only have 4 to 15 amino acids. In addition, the experimental results disclosed in the present invention prove that such repair peptides have a sustained effect on the treatment site, and thus have an advanced technical effect.

DETAILED DESCRIPTION

Hereinafter the present invention will be further described in detail in conjunction with embodiments and the drawings, but embodiments of the present invention are not limited thereto.

Experimental methods applied in the following embodiments are conventional methods without otherwise specified. All the materials and reagents applied in the embodiments are commercially available without otherwise specified. It is to be understood that the embodiments described below are intended to explain and not to limit the present invention.

Example 1

Figure 1:
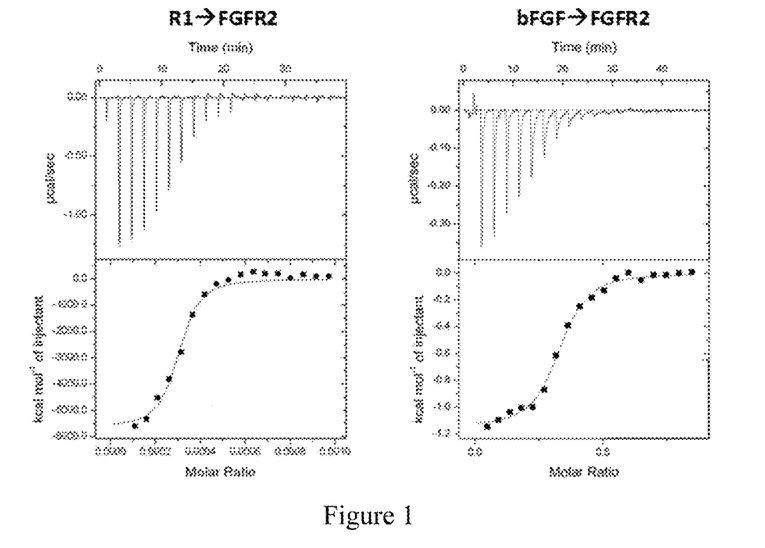
FIG. 1 is a diagram showing detection results of the affinity between the repair peptide R1 and bFGF and FGFR2 by using an ITC method.

1. Detection of the Affinity Between the Repair Peptide R1 and FGFR2 by Using the ITC Method The affinity was detected by an isothermal totration calorimetry (ITC), and the detection result was shown in FIG. 1. The affinity constant K between the repair peptide R1 and FGFR2 was $7.35E8 \pm 2.10E8$ $M^{-1}$ and the dissociation constant Kd therebetween was approximately 1.37 nM, while the affinity constant K between bFGF and FGFR2 was $1.62E5 \pm 2.50E4$ $M^{-1}$ and the dissociation constant Kd therebetween was approximately 6.17 µM. The results showed that the affinity between the repair peptide R1 and FGFR2 was much higher than that between bFGF and FGFR2, and the former was about 4,500 times than the latter. (The K denoted the affinity constant, and the Kd denoted the dissociation constant. The larger the K was and the smaller the Kd was, the stronger the affinity was).

Figure 2:
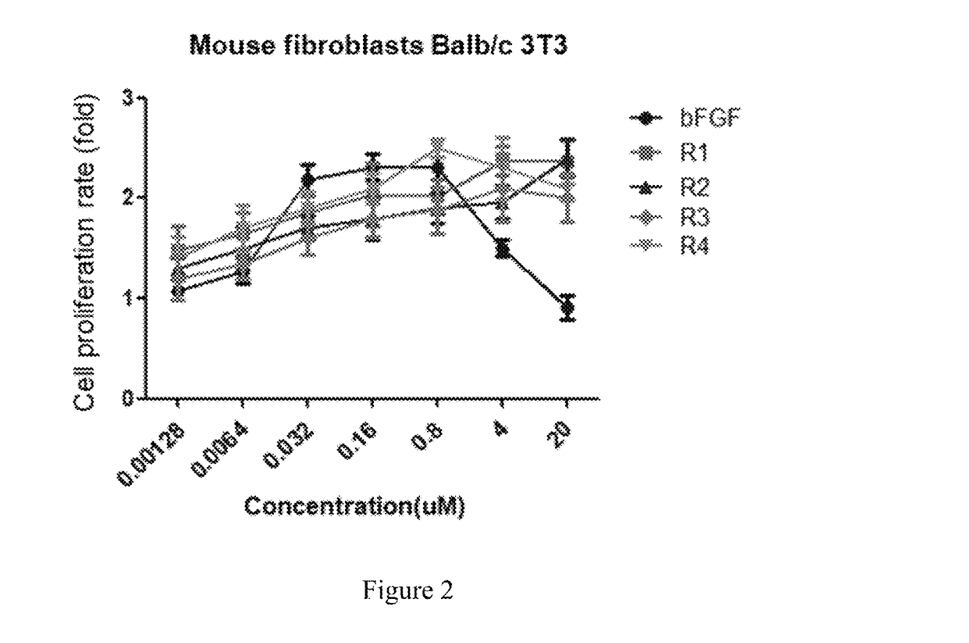
FIG. 2 is a diagram showing detection results of proliferation-promoting effects of repair peptides R1, R2, R3 and R4, and the bFGF respectively on mouse fibroblasts Balb/c 3T3 by using a CCK-8 method.

2. Detection of the Proliferation-Promoting Effects of Repair Peptides R1, R2, R3 and R4, and the bFGF Respectively on Fibroblasts Balb/c 3T3 by Using the CCK-8 Method The Ballb/c 3t3 cells were plated in 96-well plates at 4000 cells per well. After the cells were adhered and then starved for 24 hours, the cells were treated for 24 hours with the repair peptides R1, R2, R3 or R4, or the bFGF respectively at concentrations increased by 5 times. After that, the cells were treated with a CCK-8 reagent, and the optical density (OD) value of each well was detected by an enzyme-labeled instrument. As shown in FIG. 2, in lower concentration groups, the repair peptides R1, R2, R3 and R4, and the bFGF had a comparable proliferation-promoting activity, while in higher concentration groups, the cell proliferation was inhibited in the bFGF group, but the repair peptides R1, R2, R3 and R4 still had a proliferation-promoting activity. The results suggested that the above repair peptides and the bFGF promoted the fibroblast proliferation, and the repair peptides had no proliferation inhibition at high concentrations, indicating that they had a good sustained effect.

Figure 3:
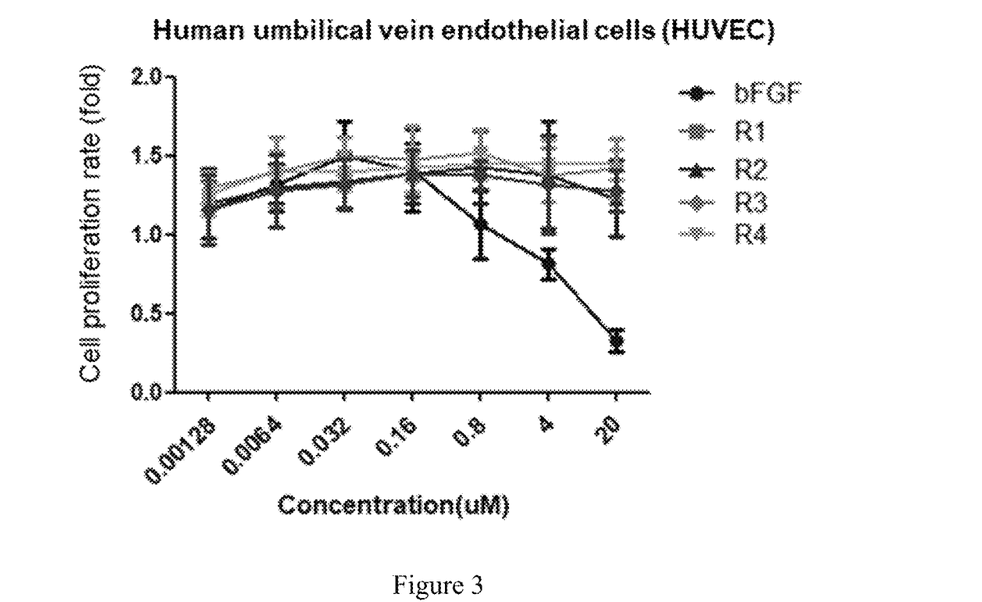
FIG. 3 is a diagram showing detection results of proliferation-promoting effects of repair peptides R1, R2, R3 and R4, and the bFGF respectively on human umbilical vein endothelial cells (HUVEC) by using the CCK-8 method.

3. Detection of the Proliferation-Promoting Effects of Repair Peptides R1, R2, R3 and R4, and the bFGF Respectively on Human Umbilical Vein Endothelial Cells (HUVEC) by Using the CCK-8 Method The HUVEC cells were plated in 96-well plates at 4000 cells per well. After the cells were adhered and then starved for 24 hours, the cells were treated for 24 hours with repair peptides R1, R2, R3 or R4, or the bFGF respectively at concentrations increased by 5 times. After that, the cells were treated with a CCK-8 reagent, and the OD value of each well was detected by an enzyme-labeled instrument. As shown in FIG. 3, in lower concentration groups (≤0.16 µM), the repair peptides R1, R2, R3 and R4, and the bFGF had a comparable proliferation-promoting activity, while in higher concentration groups, the cell proliferation was inhibited in the bFGF group, but the repair peptides R1, R2, R3 and R4 still had a proliferation-promoting activity. The results suggested that the above repair peptides promoted the growth of vascular endothelial cells, and had a good sustained effect.

4. Angiogenesis in the Chick Embryo Chorioallantoic Membrane Promoted by the Repair Peptide R1

Figure 4:
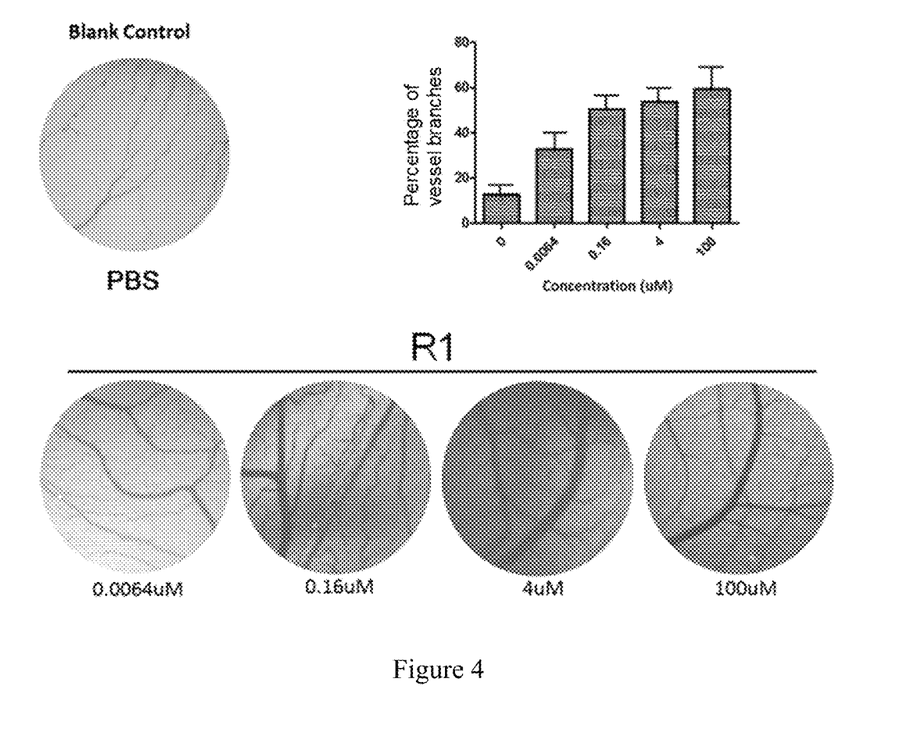
FIG. 4 is a diagram showing the angiogenesis in a chick embryo chorioallantoic membrane promoted by the repair peptide R1.

A fertilized egg cultured for 5 days was placed with the bigger head of the egg up. The eggshell was removed, and a silica gel ring was placed in the middle of the exposed chick embryo chorioallantoic membrane. 10 µL of the repair peptide R1 at concentrations increased by 25 times was respectively added drop-wise into the silica gel ring, and the opening was sealed with clean filter paper. A blank control group treated with PBS solution was set up. Further cultured for three days, then the chick embryo chorioallantoic membrane was peeled off, observed under a stereoscope and photographed, and the image was analyzed by using the software, ImageJ plus. As shown in FIG. 4, after the R1 was added, capillaries in the chick embryo chorioallantoic membrane significantly increased with the increasing dose. It was indicated that the R1 significantly promoted the angiogenesis.

5. Detection of the Angiogenesis in the Chick Embryo Chorioallantoic Membrane Promoted by Repair Peptides R1, R2, R3 and R4

Figure 5:
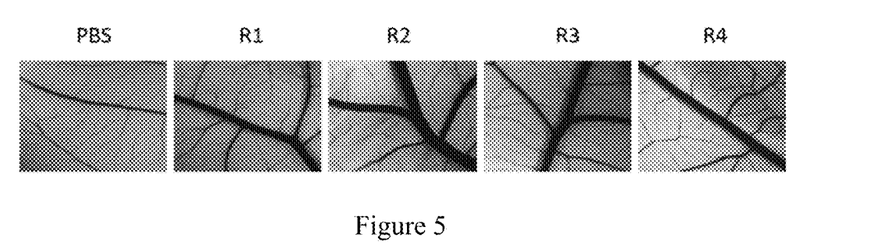
FIG. 5 is a diagram showing the angiogenesis in chick embryo chorioallantoic membranes promoted by repair peptides R1, R2, R3 and R4 at the same concentration.

A fertilized egg cultured for 5 days was placed with the bigger head of the egg up, then the eggshell was removed. 100 µL of repair peptides R1, R2, R3 and R4 at concentration of 100 ng/mL was respectively added drop-wise into the exposed chick embryo chorioallantoic membrane, and the opening was sealed with clean filter paper. A blank control group treated with PBS solution was set up. Further cultured for three days, then the chick embryo chorioallantoic membrane was peeled off, observed under a stereoscope and photographed, and the image was analyzed by using the software, ImageJ plus. As shown in FIG. 5, after repair peptide R1, R2, R3 and R4 were added, capillaries in the chick embryo chorioallantoic membrane significantly increased with the increasing dose. It was indicated that the above repair peptides promoted the angiogenesis.

6. Detection of the Wound Healing in Rat Skin Promoted by Repair Peptides R1, R2, R3 and R4

Figure 6:
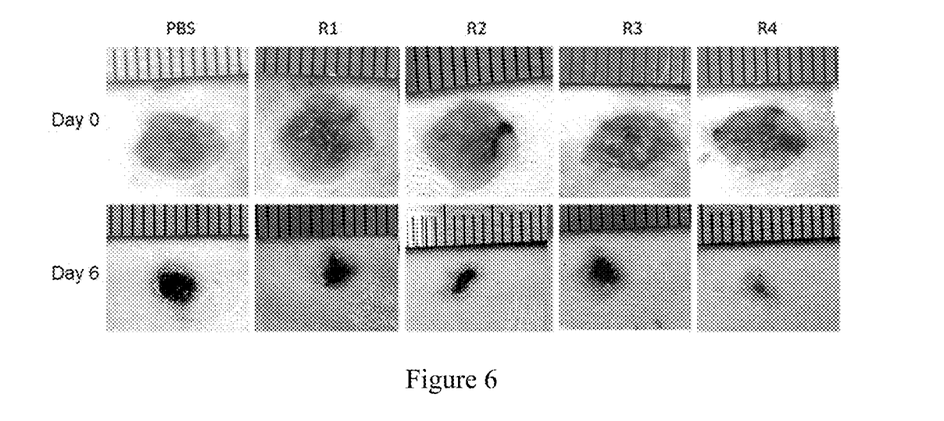
FIG. 6 is a diagram showing the wound healing in rat skin promoted by repair peptides R1, R2, R3 and R4 at the same concentration.

Balb/c mice were anesthetized by intra-peritoneal injection with 1% pentobarbital sodium (100 mg/kg), and the back was depilated and disinfected using conventional sterilization methods with 1% iodophor and 75% alcohol. Both sides of the back were cut symmetrically leaving 1-cm incisions. The incisions were sutured with two needles in the sterilized surgery. Then 10 μL of repair peptides R1, R2, R3 and R4 are respectively added drop-wise into the wounds. The wounds were open with no cotton yarn covered. A blank control group treated with PBS solution was set up. The repair peptides were added drop-wise once a day, and the wound healing was observed at the same time. As shown in FIG. 6, after the repair peptides R1, R2, R3 and R4 were added, the healing was sped up. It was indicated that the above repair peptide significantly promoted the skin wound healing and the angiogenesis in the healing site.

7. Establishment of a Rat Dorsal Root Nerve Injury Model

This model was used for detecting the influence of the drug on the recovery of the sensory function of rat peripheral nerves.

Figure 7:
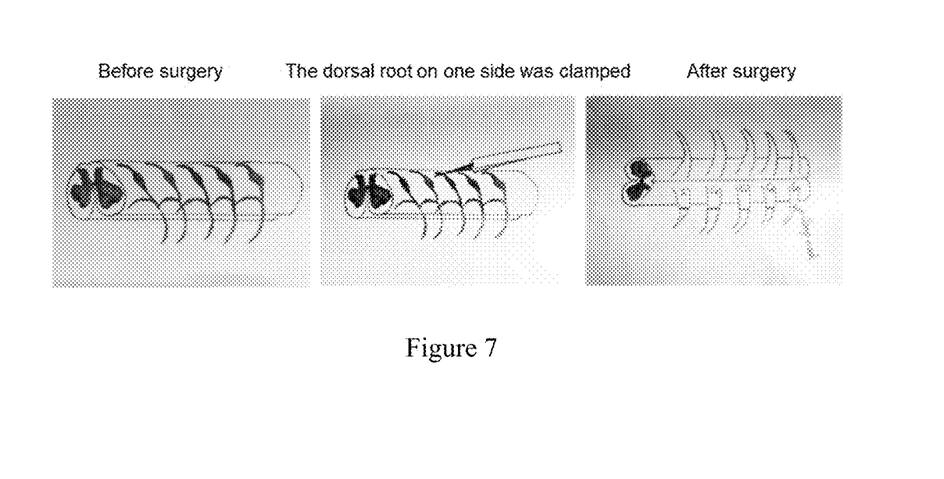
FIG. 7 is a schematic diagram showing the establishment of a rat dorsal root nerve injury model and drug treatment.

The specific method was shown in FIG. 7. The spinal cord segments from C5 to T1 of the rat were exposed through surgical operations. The dorsal roots on the right side were clamped by a tweezer at the same force, so that the dorsal roots were damaged but not broken. After that, the test drug was injected near the injury site of the rat every day for 3 weeks, i.e., 21 days.

8. Detection of the Response of Rats to Mechanical Stimulation after the Dorsal Root Nerve Injury was Repaired Respectively by Repair Peptides R1, R2, R3 and R4

The mechanical pain stimulation test is a classical method widely used to examine the sensory function of animals for neuropathic pain.

The specific method was described below. The rat was made stand on an elevated platform whose surface was wide wire meshes. Von-Frey fibers (which were very precise calibration wires) was inserted from below and passed through the mesh to puncture the lower surface of the front paws. On the door threshold, the animal quickly shook its paws off the fibers. The mechanical withdrawal threshold was defined as the minimum stimulus that caused the withdrawal response. Each foot (left front and right front) was measured 5 times, and the number of paw withdraws was recorded.

Figure 8:
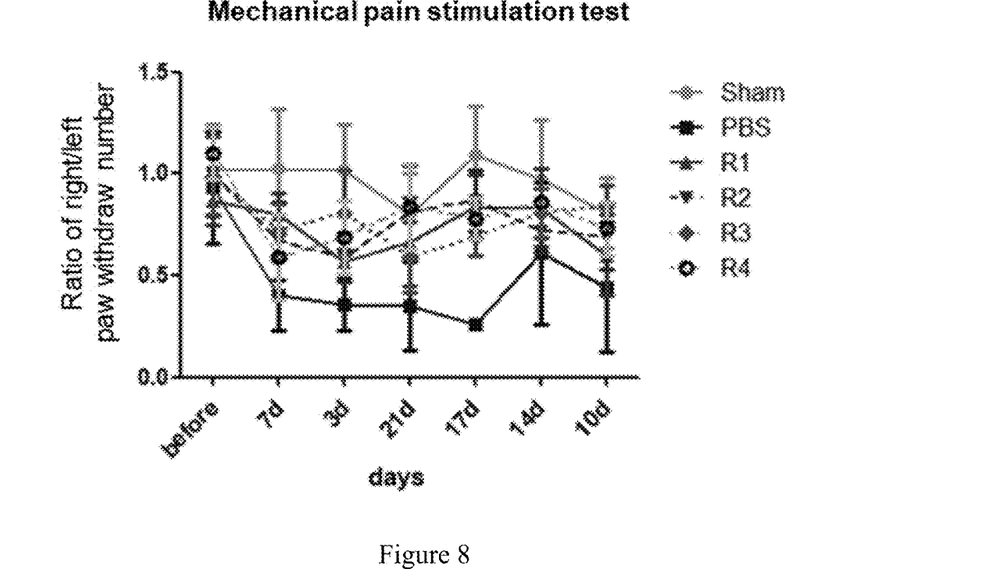
FIG. 8 shows withdrawal thresholds to mechanical stimulation in rats after the dorsal root nerve injury was repaired respectively by repair peptides R1, R2, R3 and R4. The ordinate indicated the ratio of times of right paw withdraws to left paw withdraws. A larger value represented more paw withdraws, more sensitive sensing to mechanical stimuli, and better sensory function recovery. The sham was marked as a sham operation group, the PBS was marked as a group treated with PBS solution after injury, and R1, R2, R3 and R4 were test groups treated with different repair peptides. The results showed that the repair peptide improved the response of rats to mechanical pain after injury, which indicated that the repair peptides had a significant repair effect on the dorsal root ganglion injury.

As shown in FIG. 8, the ordinate indicated the ratio of the times of right paw withdraws to left paw withdraws. A larger value represented more paw withdraws, more sensitive sensing to mechanical stimuli, and better sensory function recovery. The sham was marked as a sham operation group, the PBS was a group treated with PBS solution after trauma, and R1, R2, R3 and R4 were test groups treated with different repair peptides. The results showed that the repair peptides improved the response of rats to mechanical pain after injury, which indicated that the repair peptides had a significant repair effect on the dorsal root ganglion injury.

9. Detection of the Recovery of Response of Rats to Thermal Stimulation after the Dorsal Root Nerve Injury was Repaired Respectively by Repair Peptides R1, R2, R3 or R4

The rat was placed in a transparent plastic chamber (18×298×13 cm, 2.2 mm thick). The animal was placed 20 minutes before the test to enable the animal to adapt to the environment. A heat source was placed below the glass plate under the right or left front paw. The paw withdraw automatically activated the timer with a 0.1 second delay. The measurement was performed 3 times at a 15-minute interval and the average paw withdrawal time was recorded.

Figure 9:
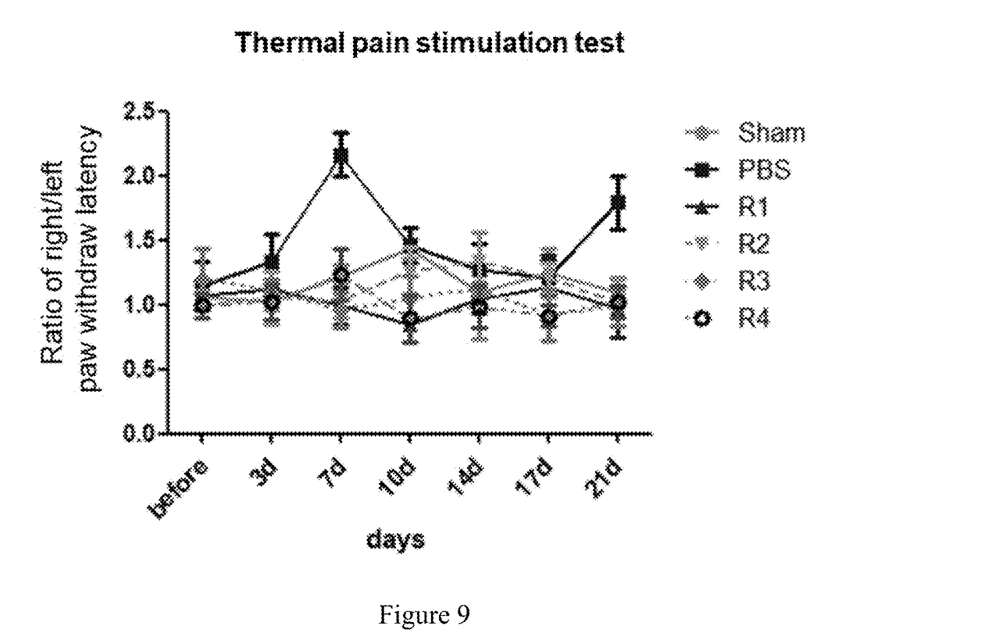
FIG. 9 shows the recovery of response to thermal pain in rats whose dorsal root nerve injury has been repaired respectively by repair peptides R1, R2, R3 and R4. The ordinate indicated the ratio of right paw withdrawal latency to left paw withdrawal latency. A smaller value represented a shorter withdrawal latency, more sensitive sensing to thermal stimuli and better sensory function recovery. The sham was marked as a sham operation group, the PBS was marked as a group treated with PBS solution, and R1, R2, R3 and R4 were test groups treated with different repair peptides. The results showed that the repair peptide improved the response of rats to thermal pain after injury, which indicated that the repair peptides had a significant repair effect on the dorsal root ganglion injury.

As shown in FIG. 9, the ordinate indicated the ratio of times of right paw withdrawal latency to left paw withdrawal latency. A smaller value represented a shorter withdrawal latency, more sensitive sensing to thermal stimuli and better sensory function recovery. The sham was marked as a sham operation group, the PBS was a group treated with PBS solution, and R1, R2, R3 and R4 were test groups treated with different repair peptides. The results showed that the repair peptide improved the response of rats to thermal pain after injury, which indicated that the repair peptides had a significant repair effect on the dorsal root ganglion injury.

10. Detection of Neuronal Axon Growth Using the Indirect Immunofluorescence

At the test time point (2 weeks or 4 weeks), the chest cavity of a deeply anesthetized rat was opened to expose the heart. The right auricle was slightly cut, and a needle was inserted into the left ventricle from the position of the cardiac apex. PBS was first pumped and then 4% PFA fixing liquid was pumped with a peristaltic pump until the liver of the rat was peach yellow in color and its body was stiff.

The C5-T1 spinal cord tissue and dorsal roots were dissected out with surgical instruments, and post-fixed in 4% PFA for 24 h, incubated overnight at 4 degrees in 15% sucrose, and further incubated overnight at 4 degrees in 30% sucrose. After embedded in the OCT, frozen sections with a thickness of 15 μm were obtained, and only sections of C7 segment tissue were collected for further experiments.

The liquid outside the prepared frozen section of the tissue was lightly wiped by filter paper, the tissue was encircled by an immunohistochemical pen, and then the tissue section was sealed in a wet box for 1 hour at room temperature with 10% donkey serum. The blocking solution outside the specimen was then gently wiped off with filter paper, and the primary antibody (1:100) diluted with 10% donkey serum was added drop-wise and incubated overnight at 4 degrees in a wet box. The primary antibody was discarded and the specimen was washed 3 times with PBS solution for 5 minutes each time. The liquid outside the specimen was wiped off with filter paper, a fluorescence-labeled secondary antibody diluted by 10% donkey serum was added drop-wise, and then the specimen was placed in a wet box and incubated for 2 hours at room temperature in the dark. The secondary antibody was pipetted out, and the specimen was washed gently 3 times with PBS solution for 5 minutes each time. The liquid outside the specimen was wiped off with filter paper, anti-fluorescence quencher containing DAPI dye solution was added drop-wise, and then the specimen was sealed with a clean cover glass and stored at 4 degrees in the dark.

The antibodies were respectively: NF200 (available from Abcam, article No.: ab40796), Lamini (available from Sigma, article No. L9393), CGRP (available from Sigma, article No. C8198). The specimen was counterstained with a fluorescent secondary antibody (available from Invitrogen), and observed under a fluorescent microscope and photographed.

The NF200 was a marker protein of nerve fibers, which could be used to observe the growth condition of neuron axons; the Laminin was a marker protein of peripheral nerve fibers, which could be used to observe the growth condition of neuron axons stimulated by the medicine; and the CGRP was associated with pain receptors that transmitted pain.

Figure 10:
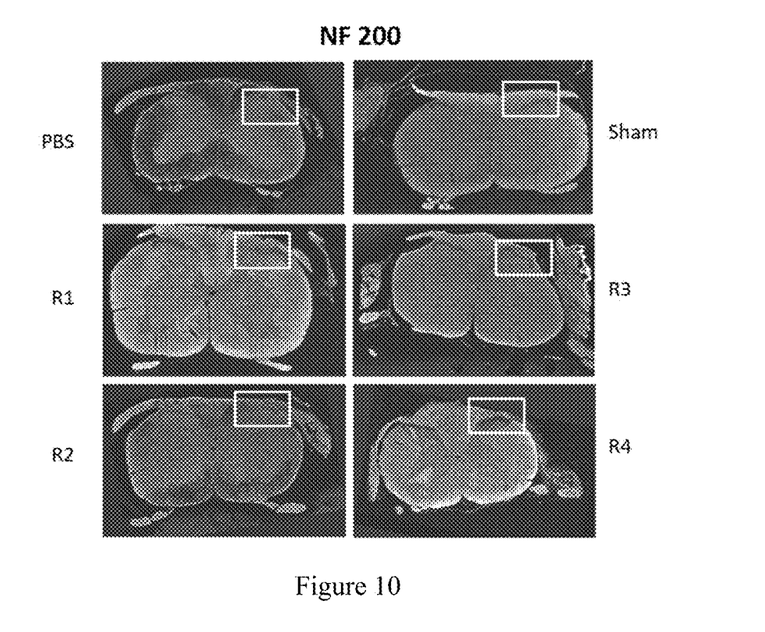
FIG. 10 shows the neuronal axon growth detected by using indirect immunofluorescence 2 weeks after the crushed dorsal root ganglion was treated with repair peptides. An antibody and a fluorescent secondary antibody against the marked protein NF200 were used. The NF200 was a marked protein of the never fiber.
Figure 11:
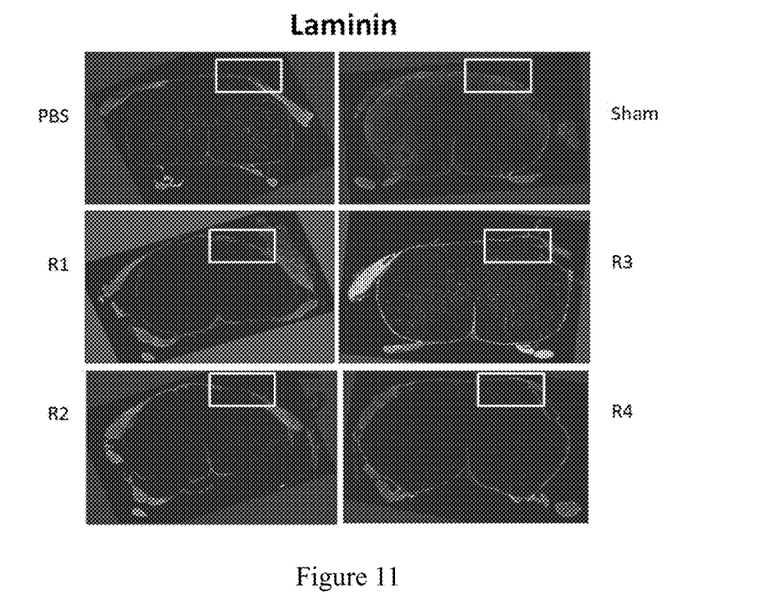
FIG. 11 shows the neuronal axon growth detected by using indirect immunofluorescence 2 weeks after the crushed dorsal root ganglion was treated with repair peptides. An antibody and a fluorescent secondary antibody against the marked protein Laminin were used. The Laminin was a marked protein of the peripheral nerve fiber; and, FIG. 12 shows the neuronal axon growth detected by using indirect immunofluorescence 2 weeks after the crushed dorsal root ganglion was treated with repair peptides. An antibody and a fluorescent secondary antibody against the marked protein CGRP were used. The CGRP protein was associated with pain receptors that transmit pain.
Figure 12:
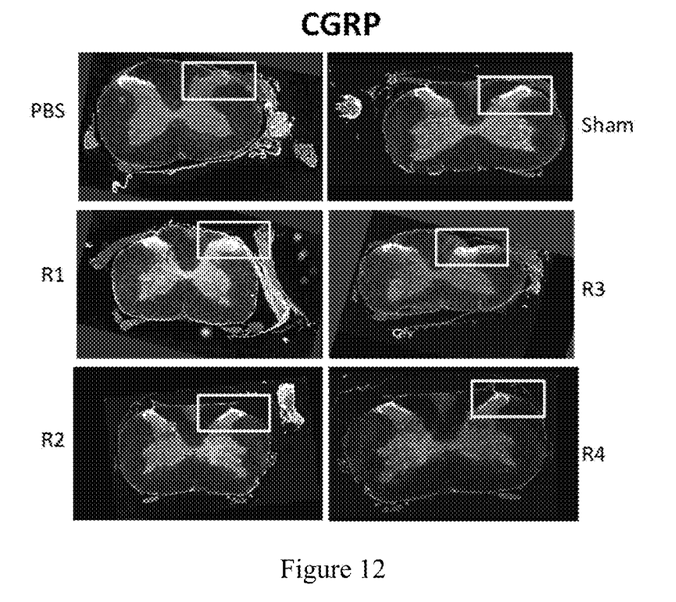

The sham was marked as a sham operation group, the PBS was a group treated by PBS solution after injury, and R1, R2, R3 and R4 were test groups treated by different repair peptides. The results were shown in FIGS. 10 to 12, and it can be seen through experimental tests that the repair peptide treatment group can significantly promote the growth of nerve synapses and the repair of damaged dorsal root nerves.

The above embodiments are only preferred embodiments of the present invention and are not intended to limit the present invention. Any other changes, modification, substitution, combination, simplification within the spirit and principle of the present invention should be regarded as an equivalent displacement of the present invention, and are included within the protection scope of the present invention.

What is claimed is:

1. A method for promoting post-traumatic tissue repair and generation, comprising administering to a subject an effective amount of a chemically synthesized repair peptide, wherein the repair peptide is a linear peptide up to 15 amino acids in length comprising the sequence of GPANVET (SEQ ID NO: 1), KVKVGPANVKVKV (SEQ ID NO: 2), GPANVEKEKEK (SEQ ID NO: 3), or CGPANVETC (SEQ ID NO: 4).

* * * * *